(12) United States Patent
Gelfand et al.

(10) Patent No.: US 10,827,965 B2
(45) Date of Patent: Nov. 10, 2020

(54) BIOLOGICAL FLUID COLLECTION DEVICE AND BIOLOGICAL FLUID SEPARATION AND TESTING SYSTEM

(71) Applicant: Becton, Dickinson and Company, Franklin Lakes, NJ (US)

(72) Inventors: Craig A. Gelfand, Jackson, NJ (US); Ashley Rachel Rothenberg, Morris Plains, NJ (US); Bradley M. Wilkinson, North Haledon, NJ (US); Daniel J. Marchiarullo, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 321 days.

(21) Appl. No.: 16/015,381

(22) Filed: Jun. 22, 2018

(65) Prior Publication Data
US 2018/0296148 A1    Oct. 18, 2018

Related U.S. Application Data

(63) Continuation of application No. 15/341,124, filed on Nov. 2, 2016, now Pat. No. 10,028,690, which is a
(Continued)

(51) Int. Cl.
*A61B 5/00* (2006.01)
*A61B 5/15* (2006.01)
(Continued)

(52) U.S. Cl.
CPC ...... *A61B 5/150213* (2013.01); *A61B 5/1411* (2013.01); *A61B 5/151* (2013.01); *A61B 5/15003* (2013.01); *A61B 5/157* (2013.01); *A61B 5/150022* (2013.01); *A61B 5/15101* (2013.01); *A61B 5/15105* (2013.01); *A61B 5/15144* (2013.01); *A61B 5/15198* (2013.01);
(Continued)

(58) Field of Classification Search
CPC ........ A61B 5/150213; A61B 5/150022; A61B 5/150221; A61B 5/150267; A61B 5/1411; A61B 5/151; A61B 5/15101; A61B 5/15103
See application file for complete search history.

(56) References Cited

U.S. PATENT DOCUMENTS 3,322,114 A    5/1967   Portnoy et al.
3,640,393 A    2/1972   Hurtig
(Continued)

FOREIGN PATENT DOCUMENTS

CN    1382966 A       12/2002
CN    101102847 A     1/2008
(Continued)

*Primary Examiner* — Max F Hindenburg
(74) *Attorney, Agent, or Firm* — The Webb Law Firm

(57) ABSTRACT

A biological fluid collection device that is adapted to receive a blood sample having a cellular portion and a plasma portion is disclosed. After collecting the blood sample, the biological fluid collection device is able to transfer the blood sample to a point-of-care testing device or a biological fluid separation and testing device. After transferring the blood sample, the biological fluid separation and testing device is able to separate the plasma portion from the cellular portion and analyze the blood sample and obtain test results.

14 Claims, 8 Drawing Sheets

Related U.S. Application Data continuation of application No. 14/251,676, filed on Apr. 14, 2014, now Pat. No. 9,517,026.

(60) Provisional application No. 61/811,918, filed on Apr. 15, 2013.

(51) Int. Cl.

| | |
|---|---|
| *G01N 33/49* | (2006.01) |
| *A61B 5/157* | (2006.01) |
| *B01L 3/00* | (2006.01) |
| *A61B 5/151* | (2006.01) |
| *A61M 1/34* | (2006.01) |
| *B04B 7/08* | (2006.01) |
| *G01N 1/28* | (2006.01) |
| *G01N 1/34* | (2006.01) |
| *G01N 1/40* | (2006.01) |
| *A61M 1/36* | (2006.01) |

(52) U.S. Cl.
CPC .. *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150442* (2013.01); *A61B 5/150748* (2013.01); *A61B 5/150755* (2013.01); *A61B 5/150778* (2013.01); *A61M 1/34* (2013.01); *A61M 1/3406* (2014.02); *A61M 1/36* (2013.01); *B01L 3/502* (2013.01); *B01L 3/5021* (2013.01); *B01L 3/50273* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150969* (2013.01); *B01L 2200/027* (2013.01); *B01L 2200/0621* (2013.01); *B01L 2200/0631* (2013.01); *B01L 2200/0684* (2013.01); *B01L 2200/10* (2013.01); *B01L 2300/0627* (2013.01); *B01L 2300/0672* (2013.01); *B01L 2300/0681* (2013.01); *B01L 2300/0803* (2013.01); *B01L 2300/0864* (2013.01); *B01L 2300/0877* (2013.01); *B01L 2400/0406* (2013.01); *B01L 2400/0409* (2013.01); *B01L 2400/0478* (2013.01); *B01L 2400/0688* (2013.01); *G01N 2001/4016* (2013.01); *G01N 2001/4088* (2013.01)

(56) References Cited

U.S. PATENT DOCUMENTS

| | | | |
|---|---|---|---|
| 4,511,349 A | 4/1985 | Nielsen et al. |
| 4,627,445 A | 12/1986 | Garcia et al. |
| 4,999,304 A | 3/1991 | Robertson |
| 5,055,203 A | 10/1991 | Columbus |
| 5,160,702 A | 11/1992 | Kopf-Sill et al. |
| 5,163,442 A | 11/1992 | Ono |
| 5,219,999 A | 6/1993 | Suzuki et al. |
| 5,242,606 A | 9/1993 | Braynin et al. |
| 5,304,348 A | 4/1994 | Burd et al. |
| 5,422,018 A | 6/1995 | Saunders et al. |
| 5,636,640 A | 6/1997 | Staehlin |
| 5,726,026 A | 3/1998 | Wilding et al. |
| 5,839,715 A | 11/1998 | Leinsing |
| 5,922,591 A | 7/1999 | Anderson et al. |
| 6,074,183 A | 6/2000 | Allen et al. |
| 6,264,619 B1 | 7/2001 | Ferguson |
| 6,506,167 B1 | 1/2003 | Ishimito et al. |
| 6,869,405 B2 | 3/2005 | Marsden |
| 7,678,580 B2 | 3/2010 | Kuriger |
| 8,114,351 B2 | 2/2012 | Degenhardt |
| 8,158,410 B2 | 4/2012 | Tang et al. |
| 8,470,588 B2 | 6/2013 | Boehm et al. |
| 8,491,840 B2 | 7/2013 | Cho et al. |
| 9,119,578 B2 | 9/2015 | Haghgooie et al. |
| 9,517,026 B2 | 12/2016 | Gelfand et al. |
| 2002/0009015 A1 | 1/2002 | Laugham, Jr. et al. |
| 2002/0143298 A1 | 10/2002 | Marsden |
| 2003/0134416 A1 | 7/2003 | Yamanishi et al. |
| 2004/0142463 A1 | 7/2004 | Walker et al. |
| 2004/0143226 A1 | 7/2004 | Marsden |
| 2004/0230216 A1 | 11/2004 | Levaughn et al. |
| 2005/0026301 A1 | 2/2005 | Petithory |
| 2005/0069459 A1 | 3/2005 | Ahn et al. |
| 2005/0214927 A1 | 9/2005 | Haley |
| 2006/0029923 A1 | 2/2006 | Togawa et al. |
| 2006/0228258 A1 | 10/2006 | Samsoondar |
| 2006/0240964 A1 | 10/2006 | Lolachi et al. |
| 2007/0031283 A1 | 2/2007 | Davis et al. |
| 2007/0160503 A1 | 7/2007 | Sethu et al. |
| 2008/0135502 A1 | 6/2008 | Pyo et al. |
| 2008/0240990 A1 | 10/2008 | Flaherty |
| 2009/0004060 A1 | 1/2009 | Omuro et al. |
| 2009/0105614 A1 | 4/2009 | Momose et al. |
| 2009/0136982 A1 | 5/2009 | Tang |
| 2009/0181411 A1 | 7/2009 | Battrell et al. |
| 2009/0204026 A1 | 8/2009 | Crawford et al. |
| 2010/0089815 A1 | 4/2010 | Zhang et al. |
| 2010/0093551 A1 | 4/2010 | Montagu |
| 2010/0198108 A1 | 8/2010 | Alden |
| 2010/0241031 A1 | 9/2010 | Lai |
| 2011/0058985 A1 | 3/2011 | Saiki et al. |
| 2011/0124130 A1 | 5/2011 | Wagner et al. |
| 2011/0124984 A1 | 5/2011 | Rostaing |
| 2011/0263030 A1 | 10/2011 | Kim |
| 2012/0152858 A1 | 6/2012 | Yang |
| 2012/0275955 A1 | 11/2012 | Haghgooie et al. |
| 2012/0277696 A1 | 11/2012 | Gonzalez-Zugasti et al. |
| 2012/0277697 A1 | 11/2012 | Haghgooie et al. |
| 2013/0026085 A1 | 1/2013 | Samsoondar |
| 2013/0052675 A1 | 2/2013 | Karlsson et al. |
| 2013/0082012 A1 | 4/2013 | Lean et al. |
| 2013/0086980 A1 | 4/2013 | Gadini et al. |
| 2013/0175213 A1 | 7/2013 | Dorrer et al. |
| 2013/0209331 A1 | 8/2013 | Rodenfels et al. |

FOREIGN PATENT DOCUMENTS

| | | |
|---|---|---|
| CN | 101332320 A | 12/2008 |
| CN | 102764133 A | 11/2012 |
| CN | 202714857 U | 2/2013 |
| DE | 202008010918 U1 | 12/2008 |
| EP | 0376168 A2 | 12/1989 |
| EP | 0747105 A2 | 6/1996 |
| EP | 1096254 A2 | 10/2000 |
| EP | 1106065 A2 | 11/2000 |
| EP | 1477804 A1 | 2/2003 |
| EP | 1627651 A2 | 8/2003 |
| EP | 1602329 A1 | 6/2005 |
| EP | 2264453 A1 | 6/2009 |
| EP | 2413138 A2 | 12/2010 |
| FR | 2929135 A1 | 10/2009 |
| FR | 2977808 A1 | 1/2013 |
| JP | 1297159 A | 11/1989 |
| JP | 7500910 A | 1/1995 |
| JP | 1503794 A | 4/1995 |
| JP | 2004150891 A | 5/2004 |
| JP | 2004354387 A | 12/2004 |
| JP | 2004361419 A | 12/2004 |
| JP | 2005270729 A | 10/2005 |
| JP | 200668384 A | 3/2006 |
| JP | 2006214955 A | 8/2006 |
| JP | 2006218447 A | 8/2006 |
| JP | 200750100 A | 3/2007 |
| JP | 2007249306 A | 9/2007 |
| JP | 2007315879 A | 12/2007 |
| JP | 2008157960 A | 7/2008 |
| JP | 2009128367 A | 6/2009 |
| JP | 2009264858 A | 11/2009 |

(56) References Cited

FOREIGN PATENT DOCUMENTS

| | | | |
|---|---|---|---|
| JP | 2010505096 | A | 2/2010 |
| JP | 2010147371 | A | 7/2010 |
| JP | 2013518276 | A | 5/2013 |
| JP | 5508709 | B2 | 6/2014 |
| KR | 1020100007809 | A | 1/2010 |
| WO | 9118656 | A1 | 12/1991 |
| WO | 9309710 | A1 | 5/1993 |
| WO | 2005018710 | A2 | 3/2005 |
| WO | 2006047831 | A1 | 5/2006 |
| WO | 2007002579 | A2 | 1/2007 |
| WO | 2009123592 | A1 | 10/2009 |
| WO | 2011040874 | A1 | 4/2011 |
| WO | 2011093602 | A2 | 8/2011 |
| WO | 2012121686 | A1 | 9/2012 |

BIOLOGICAL FLUID COLLECTION DEVICE AND BIOLOGICAL FLUID SEPARATION AND TESTING SYSTEM

CROSS-REFERENCE TO RELATED APPLICATION

The present application is a continuation of U.S. application Ser. No. 15/341,124, filed Nov. 2, 2016, entitled "Biological Fluid Collection Device and Biological Fluid Separation and Testing System", which is a continuation of U.S. application Ser. No. 14/251,676, filed Apr. 14, 2014 (now U.S. Pat. No. 9,517,026), entitled "Biological Fluid Collection Device and Biological Fluid Separation and Testing System", which claims priority to U.S. Provisional Application No. 61/811,918, filed Apr. 15, 2013, entitled "Medical Device for Collection of a Biological Sample", the entire disclosure of which is hereby incorporated by reference.

BACKGROUND OF THE INVENTION

1. Field of the Disclosure

The present disclosure relates generally to devices, assemblies, and systems adapted for use with vascular access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid collection device, such as a blood collection device, that is adapted to receive a blood sample having a cellular portion and a plasma portion. After collecting the blood sample, the biological fluid collection device is able to transfer the blood sample to a point-of-care testing device or a biological fluid separation and testing device, such as a blood separation and testing device. After transferring the blood sample, the biological fluid separation and testing device is able to separate the plasma portion from the cellular portion and analyze the blood sample and obtain test results. In one embodiment, the biological fluid collection device provides a closed system that reduces the exposure of a blood sample to both skin and environment and provides fast mixing of a blood sample with a sample stabilizer. The sample stabilizer can be an anticoagulant, or a substance designed to preserve a specific element within the blood such as, for example, RNA, protein analyte, or other element.

In accordance with an embodiment of the present invention, a biological fluid collection device includes a lancet housing having an inlet port and an interior defining a first flow channel in fluid communication with the inlet port. The device also includes a second flow channel in fluid communication with the first flow channel, and at least a portion of the second flow channel is diverted from the first flow channel. The device also includes a puncturing element which is moveable between a pre-actuated position, in which the puncturing element is retained within the interior, and a puncturing position, in which the puncturing element extends through the inlet port of the housing and provides fluid communication with the first flow channel. The device also includes a transfer cartridge having a reservoir, and the second flow channel is in fluid communication with the reservoir of the transfer cartridge.

In certain configurations, the first flow channel is adapted to receive a blood sample therein. The first flow channel may be dimensioned to receive the first blood provided to the flow channel. The first flow channel may include a reservoir region spaced apart from the inlet port, and a truncated region spaced apart from the reservoir region. The second flow channel may be provided in fluid communication with the truncated region. The transfer cartridge may be removably engageable with a portion of the housing. An internal fill volume of the reservoir may correspond to a volume of fluid required to perform a diagnostic test. At least one of the first flow channel and the second flow channel may include a vent to atmosphere.

In accordance with another embodiment of the present invention, a biological fluid separation device includes a rotatable body having a center of rotation and an outer periphery. The rotatable body has a body inlet adapted to receive a multi-component blood sample. The device also includes a separation chamber defined within the rotatable body and in fluid communication with the body inlet. The separation chamber has a chamber outlet spaced apart from the body inlet, and the separation chamber is adapted to receive the multi-component blood sample. The device also includes a blood component chamber defined within the rotatable body and in fluid communication with the chamber outlet. When a rotational force is applied to the rotatable body, a component of the multi-component blood sample passes from the separation chamber into the blood component chamber and a second component of the multi-component blood sample is retained within the separation chamber. The blood component chamber is disposed adjacent the center of rotation and the separation chamber is disposed adjacent the outer periphery of the rotatable body.

In certain configurations, the blood component is a plasma component of the multi-component blood sample and the second component is a cellular component of the multi-component blood sample. The device may also include a diagnostic chamber in fluid communication with the blood component chamber. The rotatable body may be disc-shaped. In other configurations, the blood component chamber receives the blood component of the multi-component blood sample upon the rotatable body being rotated by a processing instrument. The device may also include a diagnostic chamber in fluid communication with the blood component chamber and a detection zone readable by a processing instrument.

In accordance with another embodiment of the present invention, a biological fluid separation and testing system, such as a blood separation and testing system, for a multi-component blood sample includes a biological fluid collection device. The biological fluid collection device includes a lancet housing having an inlet port and an interior defining a first flow channel in fluid communication with the inlet port. The device also includes a second flow channel in fluid communication with the first flow channel, and at least a portion of the second flow channel is diverted from the first flow channel. The device also includes a puncturing element moveable between a pre-actuated position, wherein the puncturing element is retained within the interior, and a puncturing position, wherein the puncturing element extends through the inlet port of the housing and provides fluid communication with the first flow channel. The device further includes a transfer cartridge having a reservoir, with the second flow channel in fluid communication with the reservoir of the transfer cartridge. The system also includes a biological fluid separation device, such as a blood separation device, including a rotatable body having a center of rotation and an outer periphery. The rotatable body has a body inlet adapted to receive the multi-component blood sample. The separation device also includes a separation chamber defined within the rotatable body and in fluid communication with the body inlet. The separation chamber also has a chamber outlet spaced apart from the body inlet, with the separation chamber adapted to receive the multi-component blood sample therein. The separation device further includes a blood component chamber defined within the rotatable body and in fluid communication with the chamber outlet. When a rotational force is applied to the rotatable body, a component of the multi-component blood sample passes from the separation chamber into the blood component chamber and a second component of the multi-component blood sample is retained within the separation chamber. The blood component chamber is disposed adjacent the center of rotation and the separation chamber is disposed adjacent the outer periphery of the rotatable body, and the body inlet is engageable with the reservoir of the transfer cartridge.

In certain configurations, a portion of the rotatable body is threadably engageable with a portion of the transfer cartridge for aligning the body inlet in fluid communication with the reservoir. The first flow channel may be dimensioned to receive the first blood provided to the flow channel. The transfer cartridge may be removably engageable with a portion of the housing and subsequently engageable with a portion of the rotatable body.

In other configurations, at least one of the first flow channel and the second flow channel includes a vent to atmosphere. The system may also include a diagnostic chamber in fluid communication with the blood component chamber. In certain configurations, the blood component is a plasma component of the multi-component blood sample and the second component is a cellular component of the multi-component blood sample. The blood component chamber may receive the component of the multi-component blood sample upon the rotatable body being rotated by a processing instrument. The system may also include a diagnostic chamber in fluid communication with the blood component and including a detection zone readable by a processing instrument.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION OF THE EMBODIMENTS

Figure 1:
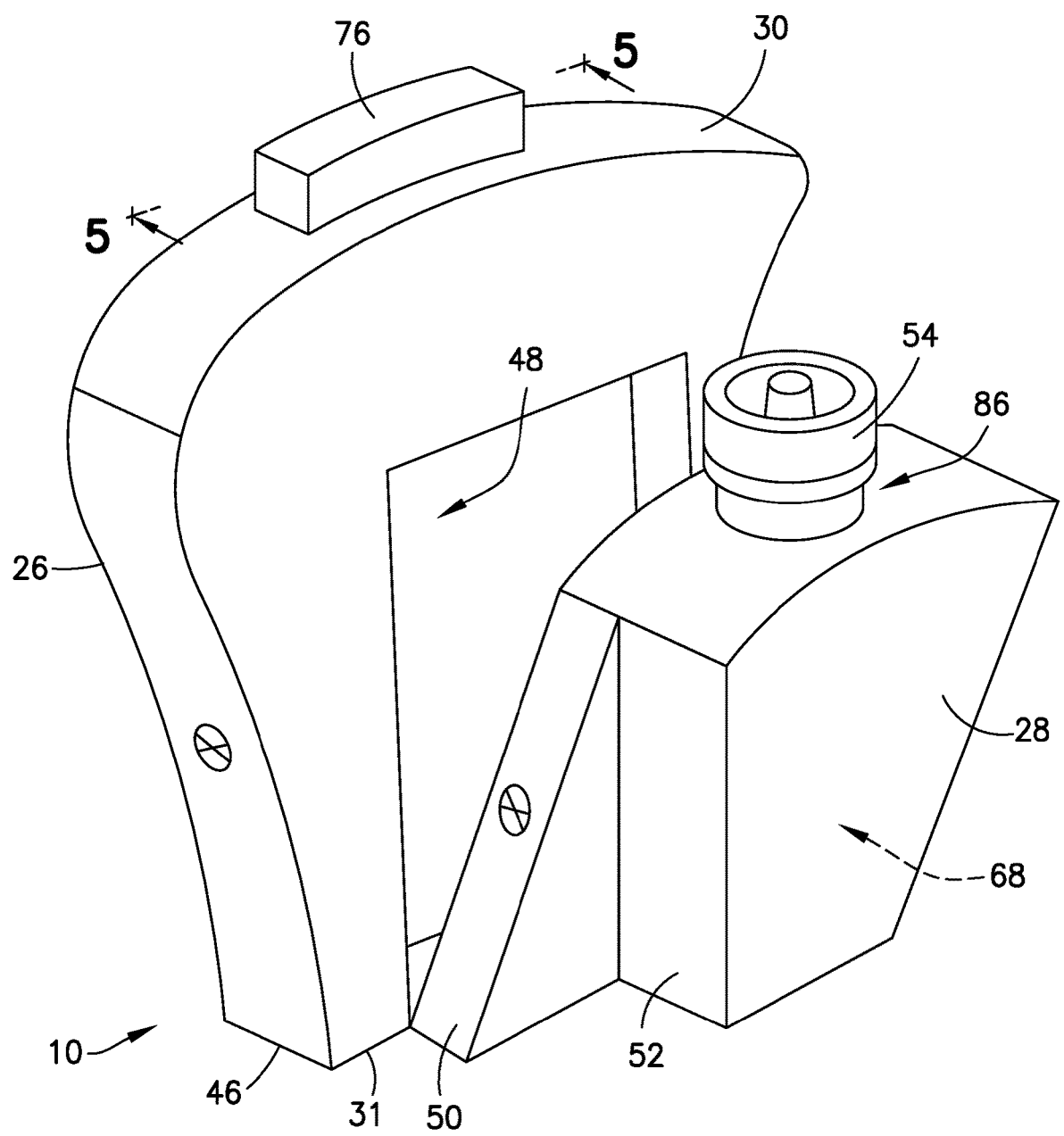
FIG. 1 is a perspective view of a biological fluid collection device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; and 4) improving the overall ease of use.

FIGS. 1-9 illustrate an exemplary embodiment of the present disclosure. Referring to FIGS. 1-9, a biological fluid collection device, such as a blood collection device 10, of the present disclosure is adapted to receive a multi-component blood sample 12 having a cellular portion 14 and a plasma portion 16.

Figure 7:
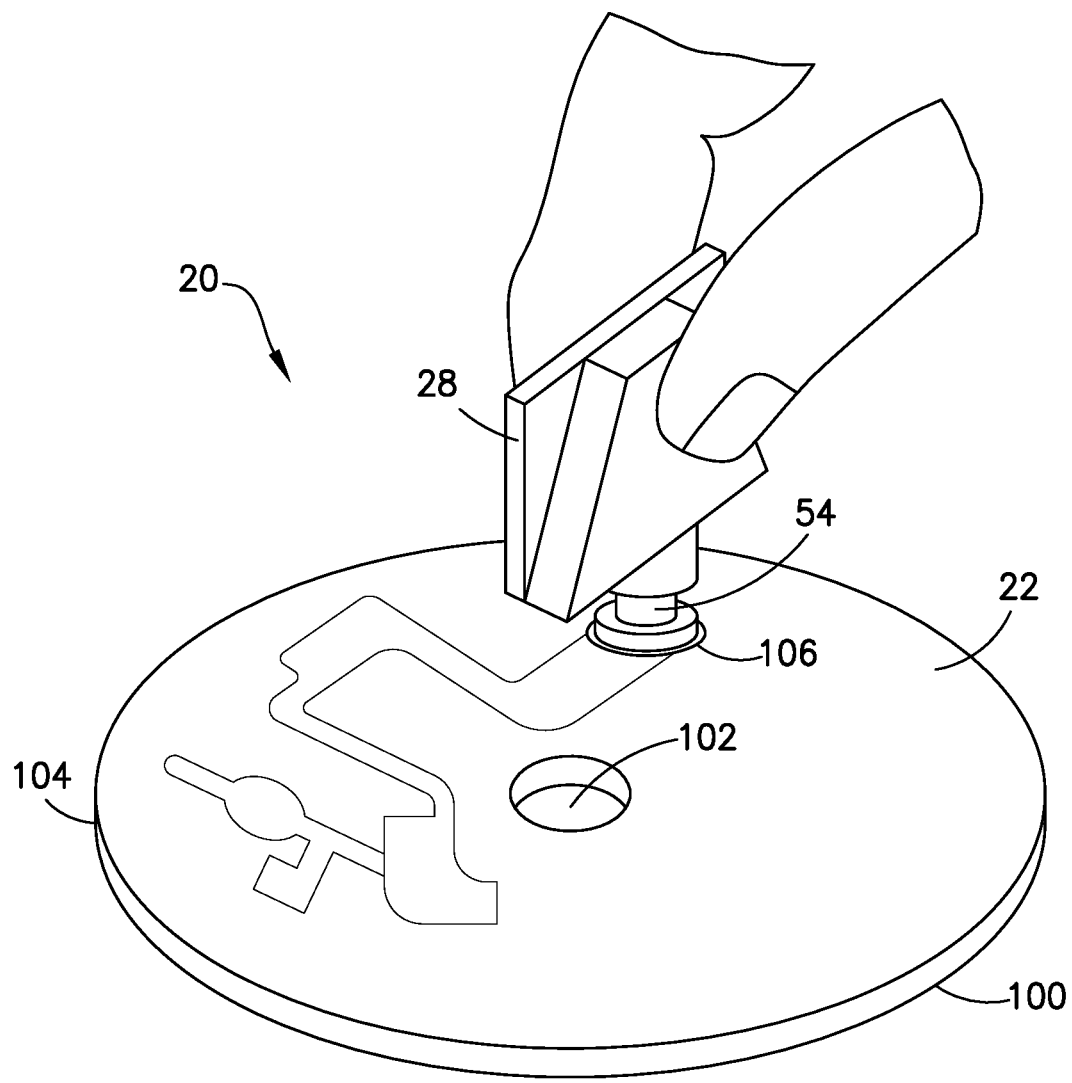
FIG. 7 is a perspective view of a transfer cartridge and a biological fluid separation and testing device in accordance with an embodiment of the present invention.

FIG. 7 illustrates an exemplary embodiment of the present disclosure. Referring to FIG. 7, a biological fluid separation and testing system, such as a blood separation and testing system 20, of the present disclosure includes a blood collection device 10 and a biological fluid separation and testing device, such as a blood separation and testing device, or point-of-care testing device 22 engageable with the blood collection device 10 for closed transfer of a blood sample 12 from the blood collection device 10 to the blood separation and testing device 22. After transferring the blood sample 12, the blood separation and testing device 22 is able to separate the plasma portion 16 from the cellular portion 14 of the multi-component blood sample and analyze the blood sample and obtain test results.

Referring to FIGS. 1-6, the blood collection device 10 includes a lancet housing 26 and a transfer cartridge 28 that is removably engageable with a portion of the lancet housing 26. The lancet housing 26 generally includes a top portion 30, a bottom portion 31, a central aperture or interior 32, an inlet port 34, a first flow channel 36, a second flow channel 38, a reservoir region 40, a truncated region 42, a puncturing element engagement portion 44, an adhesive 46 on the bottom portion 31 of the lancet housing 26, and a transfer cartridge receiving cavity 48. The inlet port 34 and the first flow channel 36 are adapted to receive a blood sample therein.

In one embodiment, the lancet housing 26 includes a diverted and vented chamber or reservoir region 40 that pulls off a first drop of blood. In one embodiment, the reservoir region 40 includes a vent or a vent hole. In another embodiment, the reservoir region 40 could contain a small sponge or a wicking material that assists in drawing a first drop of blood. In yet another embodiment, the reservoir region 40 could include a passive valve design. For example, the reservoir region 40 could include structure that would fill the reservoir region 40 first and only once the reservoir region 40 is sufficiently filled would a barrier, such as a capillary break, be overcome thereby allowing a blood sample to flow to the transfer cartridge 28. In other embodiments, the blood collection device 10 could include any mechanism that is adapted to pull a first drop of blood into the reservoir region 40 without the first drop of blood flowing to the transfer cartridge 28.

In one embodiment, the lancet housing 26 includes the first flow channel 36 that is in fluid communication with the inlet port 34 and the second flow channel 38 is in fluid communication with the first flow channel 36. In one embodiment, at least a portion of the second flow channel 38 is diverted from the first flow channel 36. In one embodiment, at least one of the first flow channel 36 and the second flow channel 38 includes a vent to atmosphere.

Figure 3:
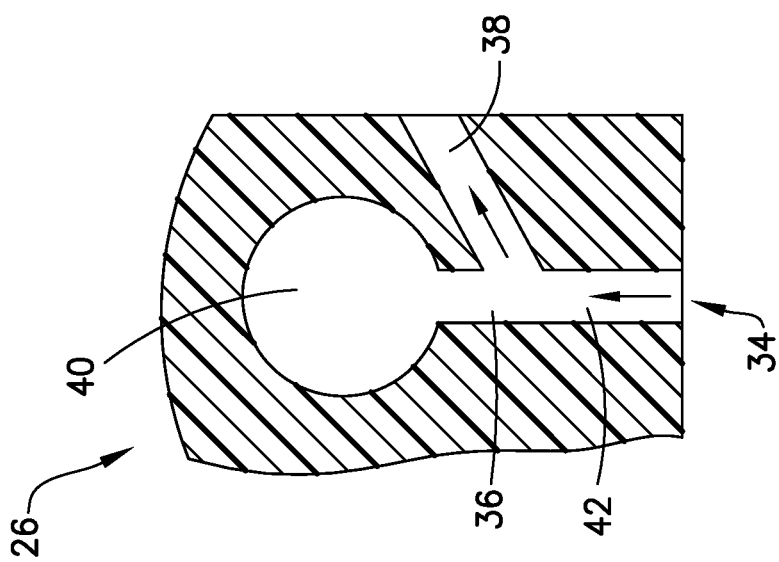
FIG. 3 is a cross-sectional view of a portion of a biological fluid collection device in accordance with an embodiment of the present invention.

Referring to FIG. 3, in one embodiment, the first flow channel 36 of the lancet housing 26 includes a reservoir region 40 that is spaced apart from the inlet port 34 and a truncated region 42 that is spaced apart from the reservoir region 40. In one embodiment, the second flow channel 38 of the lancet housing 26 is provided in fluid communication with the truncated region 42.

Figure 4:
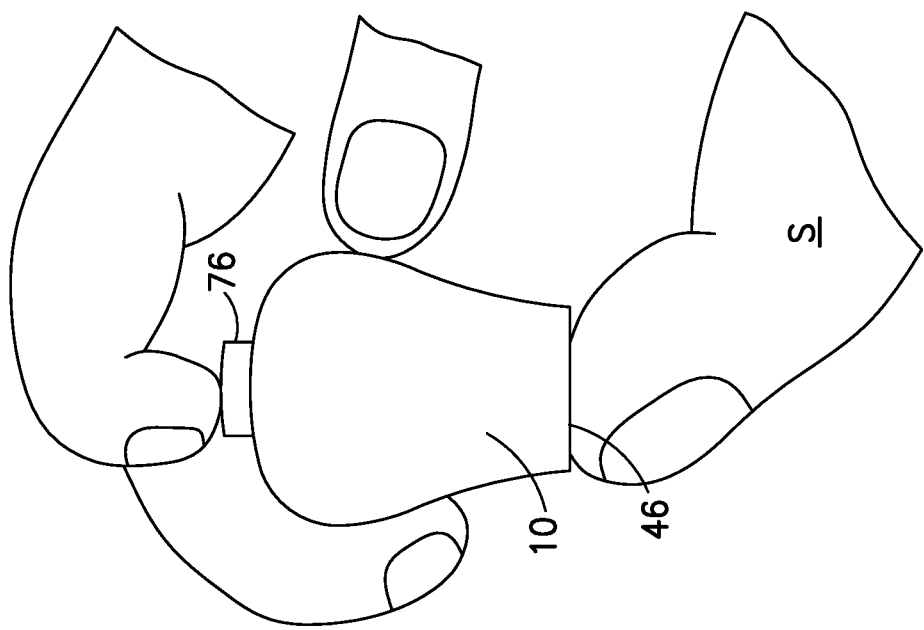
FIG. 4 is a perspective view of a biological fluid collection device in accordance with an embodiment of the present invention, with a lancet housing in a first position.
Figure 5:
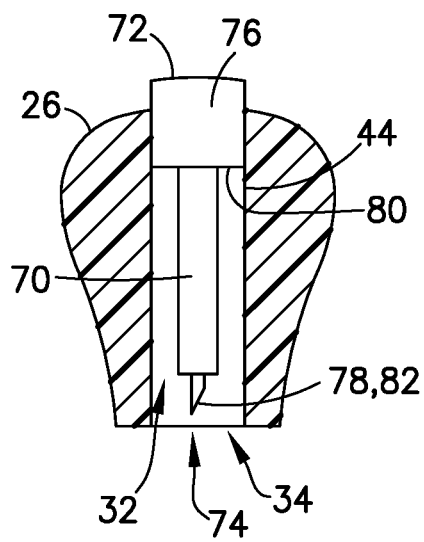
FIG. 5 is a cross-sectional view of a lancet housing in accordance with an embodiment of the present invention.
Figure 6:
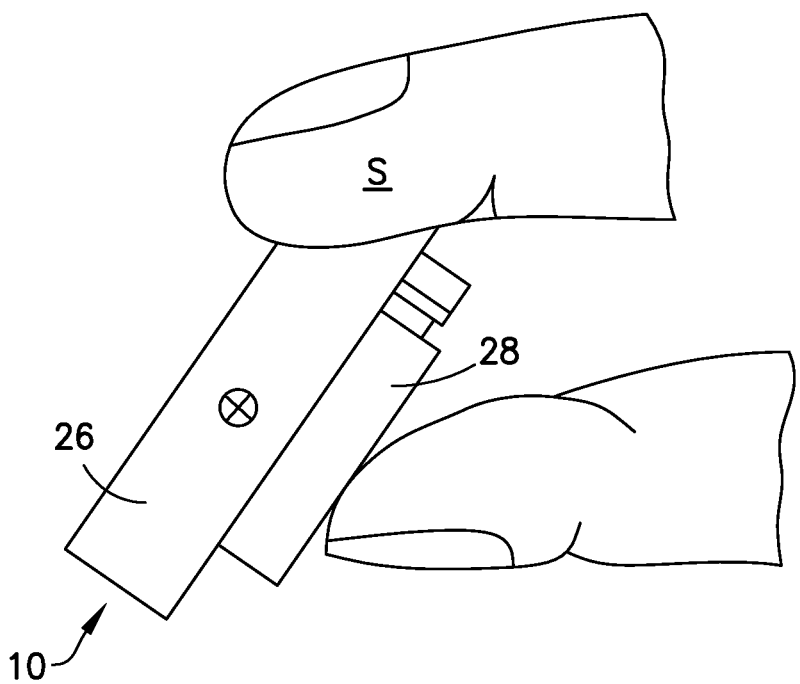
FIG. 6 is a perspective view of a biological fluid collection device in accordance with an embodiment of the present invention, with a lancet housing in a second position.

Referring to FIGS. 1-6, the blood collection device 10 also includes a puncturing element structure 70 that may be secured within the central aperture or interior 32 of the lancet housing 26. The puncturing element structure 70 generally includes a first end 72, a second end 74, a push button 76 adjacent the first end 72, a puncturing element 78 adjacent the second end 74, and a housing engagement portion 80. The housing engagement portion 80 engages the puncturing element engagement portion 44 of the lancet housing 26 for securing the puncturing element structure 70 to the lancet housing 26 within the central aperture 32 as shown in FIG. 5. The puncturing element structure 70 includes a puncturing element 78 having a puncturing end 82. The puncturing end 82 is adapted for puncturing the skin surface S of a patient (FIG. 4), and may define a pointed end, a blade edge, or a similar cutting mechanism. The puncturing end 82 may include a preferred alignment orientation, such as with a pointed end of a blade aligned in a specific orientation. In one embodiment, the puncturing element 78 comprises a micro-needle array.

The puncturing element 78 is adapted for movement between a pre-actuated position wherein the puncturing element 78 including the puncturing end 82 is retained within the interior 32 of the lancet housing 26 and a puncturing position wherein the puncturing end 82 of the puncturing element 78 extends through the inlet port 34 of the lancet housing 26 to puncture a skin surface S of a patient to draw a blood sample 12. In one embodiment, actuation of the push button 76 moves the puncturing element 78 from the pre-actuated position to the puncturing position.

In one embodiment, the lancet housing 26 of the blood collection device 10 may include a self-sealing dock that would allow an external lancet or puncturing element to be removably received within the lancet housing 26. The external lancet or puncturing element could be either pre-integrated into the packaged blood collection device 10 or introduced separately by a user before using the blood collection device 10 of the present disclosure.

Referring to FIGS. 1-4, the bottom portion 31 of the lancet housing 26 includes an adhesive or adhesive layer 46 so that the blood collection device 10 can be secured onto a skin surface S of a patient where a blood sample will be accessed. In one embodiment, the adhesive 46 of the bottom portion 31 is protected by a peel-off layer, similar to an adhesive bandage, which would be removed before placing the blood collection device 10 on the skin surface S of the patient's body. A hydrogel or other layer could be included to provide some thickness to the bottom portion 31 and help improve the stability of the adhesive seal. Additionally, in one embodiment, the adhesive 46 could include a chemistry to create a more liquid-tight seal, similar to painter's tape technology, where wetting from the paint itself causes a chemical reaction with the adhesive 46 to create a more water-tight barrier to prevent the paint from seeping under the tape. Importantly, the adhesive provides for proper adhesion of the lancet housing 26 to the skin surface S of a patient and minimizes skin contact which leads to a better sample for coagulation testing. The adhesive 46 of the lancet housing 26 can be punctured by the puncturing element 78 such that the blood evolving from the wound beneath passes through the cut into the lancet housing 26 to be collected inside the blood collection device 10.

Referring to FIGS. 1-11, the transfer cartridge 28 includes a first wall portion 50, a second wall portion 52, a transfer port 54, a reservoir 68, and a valve or septum 86 at the transfer port 54. In one embodiment, an internal fill volume of the reservoir 68 of the transfer cartridge 28 corresponds to a volume of fluid required to perform a diagnostic test.

The transfer port 54 of the transfer cartridge 28 may include a valve or septum 86 that is transitionable between a closed position and an open position. With the valve 86 in an open position, the blood sample 12 may flow through the reservoir 68 of the transfer cartridge 28 to a blood separation and testing device 22 as described in more detail below.

Figure 2:
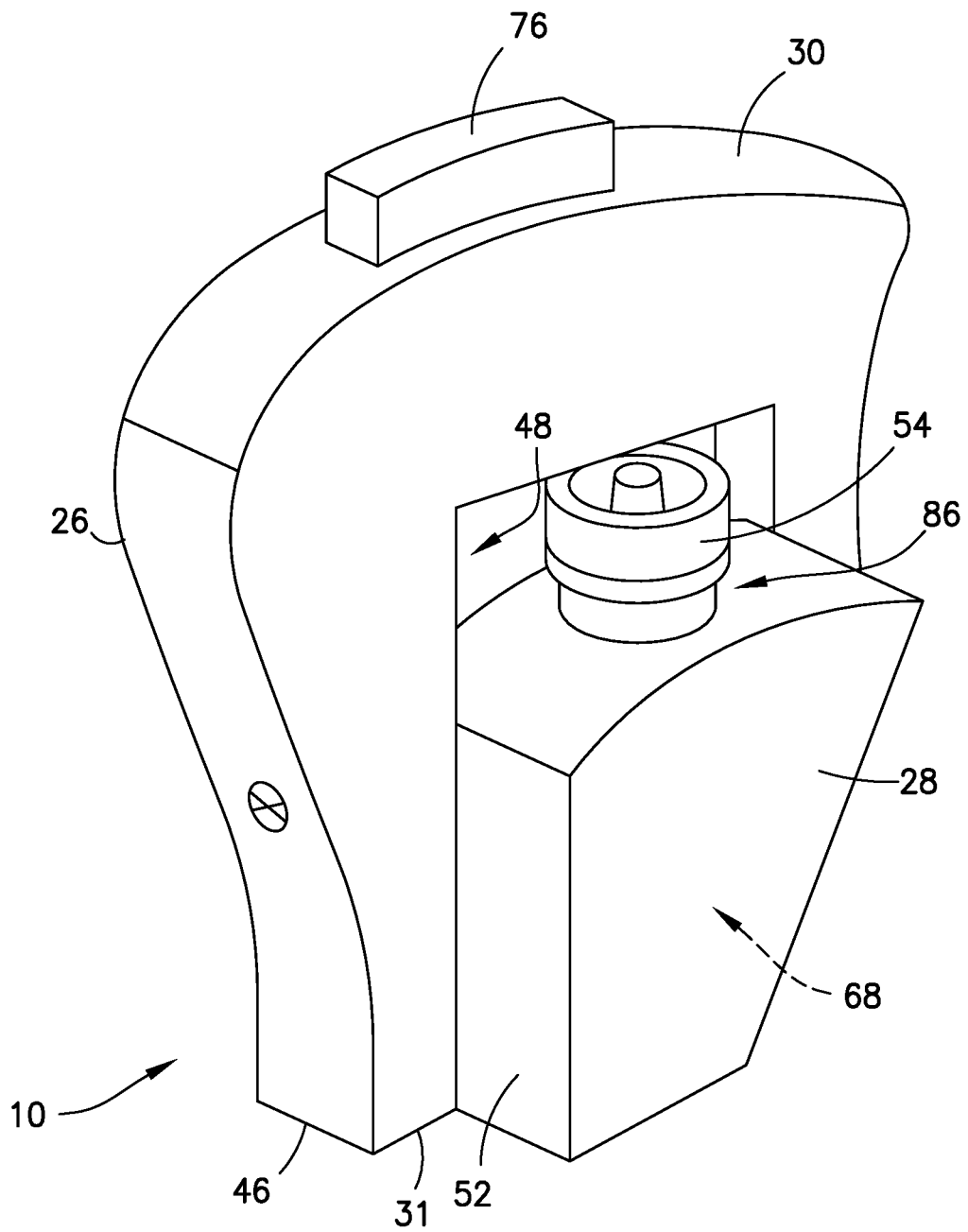
FIG. 2 is an assembled, perspective view of a biological fluid collection device in accordance with an embodiment of the present invention, with a transfer cartridge received within a portion of a lancet housing.

Referring to FIG. 2, a portion of the transfer cartridge 28 can be received within the transfer cartridge receiving cavity 48 of the lancet housing 26. In this initial position, the second flow channel 38 of the lancet housing 26 is in fluid communication with the reservoir 68 of the transfer cartridge 28 so that a collected blood sample 12 can flow through the inlet port 34 of the lancet housing 26 to the reservoir 68 of the transfer cartridge 28. When the reservoir 68 of the transfer cartridge 28 is filled with a blood sample 12, the clinician or patient can remove the transfer cartridge 28 from the lancet housing 26 as shown in FIG. 1. When removed, the reservoir 68 of the transfer cartridge 28 and all flow channels of the lancet housing 26 are sealed from the external environment.

In one embodiment, with the transfer cartridge 28 received within the transfer cartridge receiving cavity 48 of the lancet housing 26, the first wall portion 50 is received within the transfer cartridge receiving cavity 48 and the second wall portion 52 of the transfer cartridge 28 extends outward from the transfer cartridge receiving cavity 48. In this manner, the second wall portion 52 of the transfer cartridge 28 can be grasped by a user to remove the transfer cartridge 28 from the lancet housing 26.

The blood collection device 10 may also include a layer of sample stabilizer. For example, in one embodiment, a blood sample 12 that is collected within the blood collection device 10 may be exposed to and mixed with a sample stabilizer in a portion of the lancet housing 26 or the transfer cartridge 28. The sample stabilizer can be an anticoagulant, or a substance designed to preserve a specific element within the blood such as, for example, RNA, protein analyte, or other element. In one embodiment, the sample stabilizer may be disposed in a portion of the lancet housing 26. In another embodiment, the sample stabilizer may be disposed in a portion of the transfer cartridge 28 or any other area of the blood collection device 10 in which it contacts a blood sample.

Figure 8:
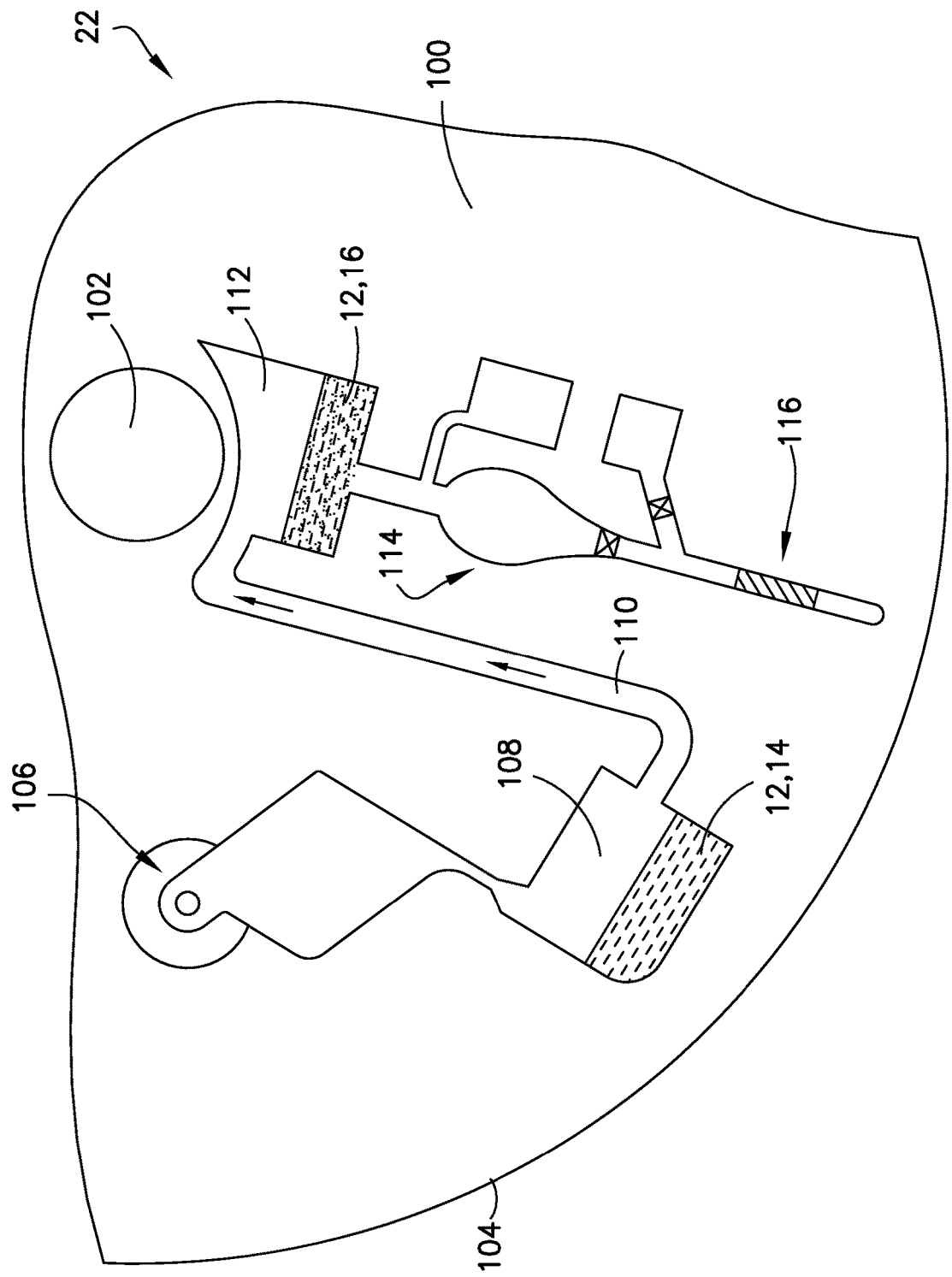
FIG. 8 is an elevation view of a biological fluid separation and testing device in accordance with an embodiment of the present invention.
Figure 9:
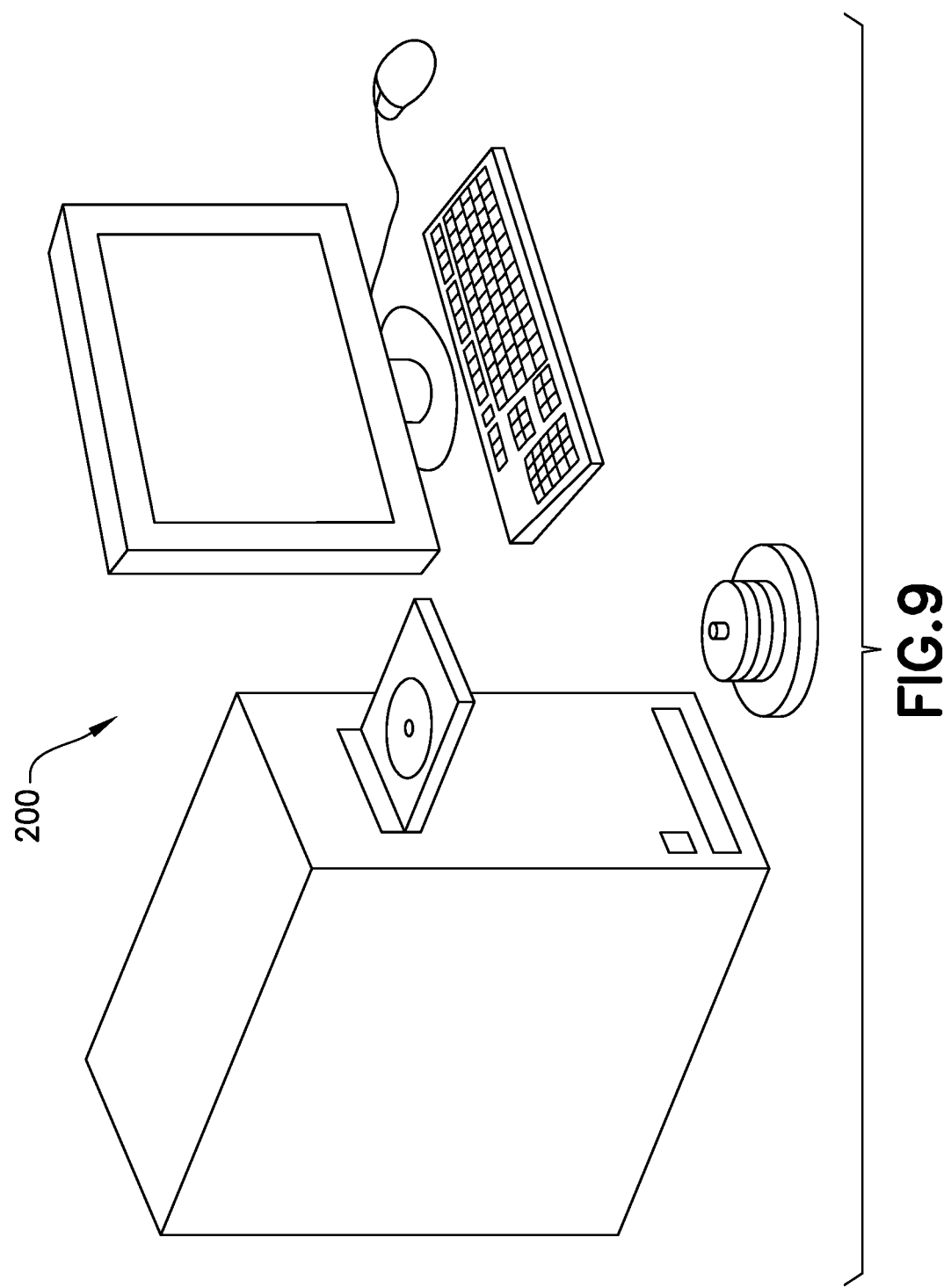
FIG. 9 is a perspective view of a processing and analyzing instrument in accordance with an embodiment of the present invention.

Referring to FIGS. 7 and 8, a blood separation and testing device or point-of-care testing device 22 includes a rotatable body 100 having a center of rotation 102 and an outer periphery 104, a body inlet or receiving port 106, a separation chamber 108, a flow channel 110, a blood component chamber, such as a plasma chamber 112, and a diagnostic portion or diagnostic chamber 114 in fluid communication with the plasma chamber 112. In one embodiment, the diagnostic chamber includes a detection zone 116 that is readable by a processing and analyzing instrument 200 (FIG. 9). In one embodiment, the rotatable body 100 is disc-shaped.

The receiving port or body inlet 106 is adapted to receive the valve 86 of the transfer port 54 of the transfer cartridge 28. The blood separation and testing device 22 is adapted to receive the valve 86 of the transfer port 54 of the transfer cartridge 28 for closed transfer of a portion of the blood sample 12 from the reservoir 68 of the transfer cartridge 28 to the blood separation and testing device 22. The blood separation and testing device 22 is able to separate the plasma portion 16 from the cellular portion 14 and analyze the blood sample 12 and obtain test results.

The separation chamber 108 is defined within the rotatable body 100 and is in fluid communication with the body inlet 106 and the separation chamber 108 includes a chamber outlet or flow channel 110 spaced apart from the body inlet 106. The separation chamber 108 is adapted to receive both the cellular portion 14 and the plasma portion 16 therein.

The blood component chamber, such as the plasma chamber 112, is defined within the rotatable body 100 and is in fluid communication with the separation chamber 108 via the flow channel or chamber outlet 110. When a rotational force is applied to the rotatable body 100, the plasma portion 16 passes from the separation chamber 108 into the plasma chamber 112 and the cellular portion 14 is retained within the separation chamber 108. In one embodiment, the plasma chamber 112 receives the plasma portion 16 of the blood sample 12 upon the rotatable body 100 being rotated by a processing and analyzing instrument 200. In one embodiment, the plasma chamber 112 is disposed adjacent the center of rotation 102 and the separation chamber 108 is disposed adjacent the outer periphery 104 of the rotatable body 100.

Once a blood sample 12 is received into the blood separation and testing device 22, the blood separation and testing device 22 may be inserted into a processing and analyzing instrument 200 that processes and analyzes the blood sample 12. First, the blood separation and testing device 22 is spun at a high rate and the plasma portion 16 is separated from the cellular portion 14 in the separation chamber 108. Then, the speed is slowed down to drive the plasma portion 16 to the plasma chamber 112 in a central portion of the blood separation and testing device 22. The plasma portion 16 can then be processed inline through the diagnostic portion 114 of the blood separation and testing device 22. Since the blood separation and testing device 22 may be of a compact disc format, the detection zone 116 is read by the internal laser of the processing and analyzing instrument 200 while it is still spinning or running.

Referring to FIG. 7, a blood separation and testing device 22 includes a receiving port or body inlet 106 adapted to receive the transfer port 54 of the transfer cartridge 28. The blood separation and testing device 22 is adapted to receive the transfer port 54 of the transfer cartridge 28 for closed transfer of a portion of the blood sample 12 from the reservoir 68 of the transfer cartridge 28 to the blood separation and testing device 22. The blood separation and testing device 22 is able to separate the plasma portion 16 from the cellular portion 14 and analyze the blood sample 12 and obtain test results.

As discussed above, the transfer port 54 of the transfer cartridge 28 may include a valve or septum 86 that is transitionable between a closed position and an open position. With the valve or septum 86 in an open position (FIG. 11), the blood sample 12 may flow through the transfer port 54 to the body inlet 106 of the blood separation and testing device 22.

Figure 11:
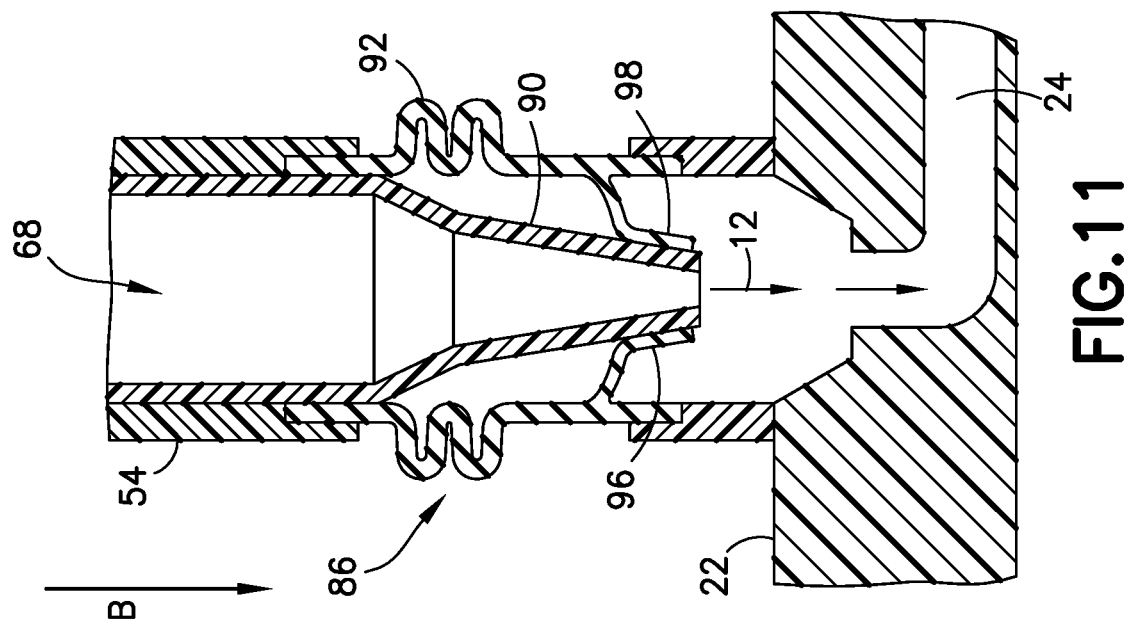
FIG. 11 is a cross-sectional view of a valve of a transfer cartridge in accordance with an embodiment of the present invention, with the valve in an open position.
Figure 10:
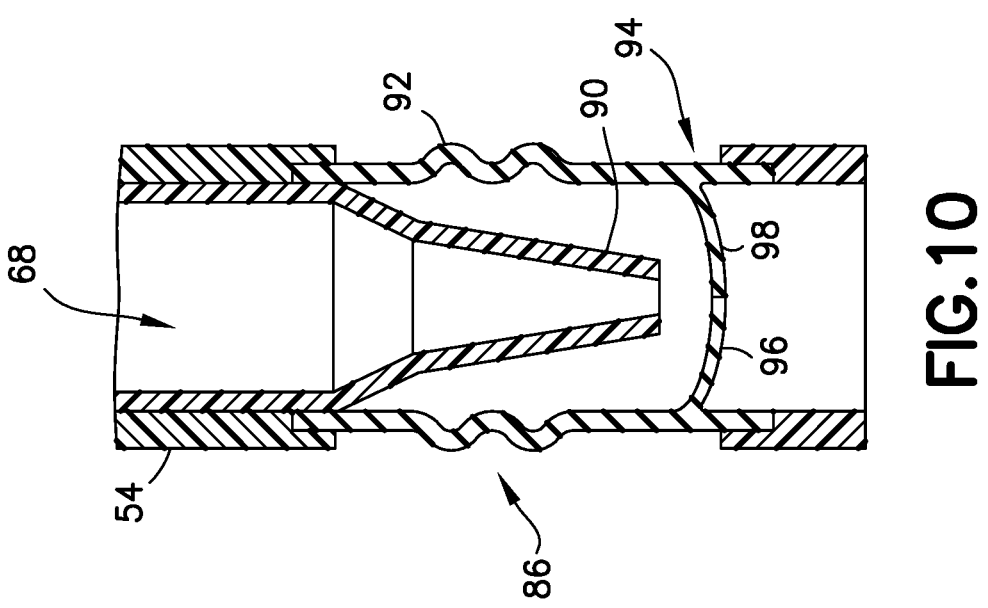
FIG. 10 is a cross-sectional view of a valve of a transfer cartridge in accordance with an embodiment of the present invention, with the valve in a closed position.

In one embodiment, referring to FIGS. 10 and 11, the valve 86 may generally include a transfer channel 90, a bellows or deformable wall member 92, and a septum or barrier 94 having a first barrier wall 96 and a second barrier wall 98. Referring to FIG. 10, the valve 86 is in a closed position to prevent the blood sample 12 from flowing through the transfer port 54. In this manner, the blood sample 12 is sealed within the transfer cartridge 28. Referring to FIG. 11, the valve 86 is in an open position so that the blood sample 12 may flow through the transfer port 54 to a blood separation and testing device 22.

Referring to FIG. 11, with the blood sample 12 received within the transfer port 54 of the transfer cartridge 28, the transfer port 54 of the transfer cartridge 28 is then positioned over the receiving port or body inlet 106 of the blood separation and testing device 22. Pushing down in the direction of arrow B compresses the deformable wall member 92 and opens up the first barrier wall 96 and the second barrier wall 98 of the septum 94 as shown in FIG. 11. With the valve 86 in the open position, the blood sample 12 is allowed to flow through the transfer port 54 and to the blood separation and testing device 22 in a closed manner reducing exposure to the clinician and the patient.

The valve 86 of the transfer cartridge 28 only opens when the transfer port 54 is pressed upon the receiving port 106 of the blood separation and testing device 22. This releases the blood sample 12 directly into the receiving port 106 of the blood separation and testing device 22, thus mitigating unnecessary exposure to the patient's blood.

In one embodiment, a portion of the rotatable body 100 of the blood separation and testing device 22 is threadably engageable with a portion of the transfer cartridge 28 for aligning the body inlet 106 in fluid communication with the reservoir 68 of the transfer cartridge 28.

Referring to FIGS. 1-11, use of a blood collection device of the present disclosure will now be described. Referring to FIG. 4, upon selecting a site, a clinician can adhere the adhesive 46 on the bottom portion 31 of the lancet housing 26 onto a skin surface S of a patient where a blood sample will be accessed over a selected sampling site.

Next, the push button 76 on the blood collection device 10 is depressed or actuated to move the puncturing element 78 from the pre-actuated position to the puncturing position so that the puncturing element 78 punctures the skin surface S of a patient. Thereafter, referring to FIG. 6, the blood collection device 10 is rolled back to collect a blood sample 12 into the reservoir 68 of the transfer cartridge 28 via the inlet port 34 of the lancet housing 26. In one embodiment, the blood sample 12 is exposed to and mixed with a sample stabilizer in a portion of the lancet housing 26 or the transfer cartridge 28. The sample stabilizer can be an anticoagulant, or a substance designed to preserve a specific element within the blood such as, for example, RNA, protein analyte, or other element.

When the reservoir 68 of the transfer cartridge 28 is filled, the clinician or patient can remove the transfer cartridge 28 from the lancet housing 26 as shown in FIG. 1. When removed, the reservoir 68 of the transfer cartridge 28 and all flow channels of the lancet housing 26 are sealed from the external environment.

Referring to FIG. 7, the next step of the process involves insertion of the transfer cartridge 28 into a blood separation and testing device 22 to transfer a blood sample from the transfer cartridge 28 to the blood separation and testing device 22. In one embodiment, the blood separation and testing device 22 may be a compact disc separation and testing system that is utilized as a point-of-care testing device.

Referring to FIGS. 7 and 11, the transfer port 54 of the transfer cartridge 28 is positioned over the receiving port or body inlet 106 of the blood separation and testing device 22. Pushing down in the direction of arrow B compresses the deformable wall member 92 and opens up the first barrier wall 96 and the second barrier wall 98 of the septum 94 as shown in FIG. 11. With the valve 86 in the open position, the blood sample 12 is allowed to flow through the transfer port 54 and to the blood separation and testing device 22 in a closed manner reducing exposure to the clinician and the patient. The valve 86 of the transfer cartridge 28 only opens when the transfer port 54 is pressed upon the receiving port 106 of the blood separation and testing device 22. This releases the blood sample 12 directly into the receiving port 106 of the blood separation and testing device 22, thus mitigating unnecessary exposure to the patient's blood.

Once a blood sample 12 is received into the blood separation and testing device 22, the blood separation and testing device 22 may be inserted into a processing and analyzing instrument 200 that processes and analyzes the blood sample 12. First, the blood separation and testing device 22 is spun at a high rate and the plasma portion 16 is separated from the cellular portion 14 in the separation chamber 108. Then, the speed is slowed down to drive the plasma portion 16 to the plasma chamber 112 in a central portion of the blood separation and testing device 22. The plasma portion 16 can then be processed inline through the diagnostic portion 114 of the blood separation and testing device 22. Since the blood separation and testing device 22 may be of a compact disc format, the detection zone 116 is read by the internal laser of the processing and analyzing instrument 200 while it is still spinning or running.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid collection device, comprising:
   a lancet housing having an inlet port and an interior defining a first flow channel in fluid communication with the inlet port, a second flow channel in fluid communication with the first flow channel, and a chamber spaced apart from the inlet, wherein at least a portion of the second flow channel is diverted from the first flow channel;
   a puncturing element moveable between a pre-actuated position wherein the puncturing element is retained within the interior of the housing and a puncturing position wherein the puncturing element extends through the inlet port of the housing and provides fluid communication with the first flow channel; and
   a transfer cartridge having a reservoir, wherein the first flow channel is in fluid communication with the chamber, and the second flow channel is in fluid communication with the reservoir of the transfer cartridge.

2. The biological fluid collection device of claim 1, wherein the chamber is dimensioned to receive the first blood provided to the first flow channel through the inlet port.

3. The biological fluid collection device of claim 1, wherein the chamber is vented.

4. The biological fluid collection device of claim 1, wherein the chamber contains a wicking material.

5. The biological fluid collection device of claim 1, further comprising a passive valve between the first flow channel and the chamber.

6. The biological fluid collection device of claim 1, further comprising a dock for removably receiving the puncturing element within the lancet housing.

7. The biological fluid collection device of claim 1, further comprising an adhesive on a bottom portion of the housing surrounding the inlet port.

8. The biological fluid collection device of claim 7, wherein the adhesive covers the inlet port and the puncturing element punctures the adhesive when the puncturing element moves from the pre-actuated position to the puncturing position.

9. The biological fluid collection device of claim 1, further comprising a transfer port in fluid communication with the reservoir.

10. The biological fluid collection device of claim 9, wherein the transfer port includes a valve transitionable between a closed position and an open position.

11. The biological fluid collection device of claim 1, further comprising a sample stabilizer in at least a portion of at least one of the housing and the transfer cartridge that contacts the biological fluid.

12. The biological fluid collection device of claim 1, wherein the transfer cartridge is removably engageable with a portion of the housing.

13. The biological fluid collection device of claim 1, wherein an internal fill volume of the reservoir corresponds to a volume of fluid required to perform a diagnostic test.

14. The biological fluid collection device of claim 1, wherein at least one of the first flow channel and the second flow channel have a vent to atmosphere.

* * * * *